United States Patent [19]

Krivan et al.

[11] Patent Number: 5,089,479
[45] Date of Patent: Feb. 18, 1992

[54] ADHESION OF MYCOPLASMA PNEUMONIAE AND MYCOPLASMA HOMINUS TO SULFATIDE

[76] Inventors: Howard C. Krivan, 14442 Parkvale Rd., Apt. 5, Rockville, Md. 20853; Victor Ginsburg, 6905 Loch Lomond Dr., Bethesda, Md. 20817; David D. Roberts, 13401 Tangier Pl., Rockville, Md. 20853

[21] Appl. No.: 277,634

[22] Filed: Nov. 28, 1988

[51] Int. Cl.$^5$ .............. A61K 31/95; A61K 31/70
[52] U.S. Cl. .......................... 514/25; 514/54; 514/59; 536/4.1; 536/112; 435/101; 435/103; 435/177; 435/176; 435/182; 435/800; 435/870
[58] Field of Search ............... 536/112, 4.1; 514/59, 514/54, 25; 435/800, 870, 176, 177, 182, 101, 103

[56] References Cited

U.S. PATENT DOCUMENTS

| | | | |
|---|---|---|---|
| 3,668,075 | 6/1972 | Cekoric et al. | 435/800 |
| 4,330,622 | 5/1982 | Desai | 435/800 |
| 4,543,328 | 9/1985 | Keller et al. | 435/800 |
| 4,590,181 | 5/1986 | McCarthy | 536/112 |
| 4,632,902 | 12/1986 | Waters et al. | 435/803 |
| 4,652,518 | 3/1987 | Makela et al. | 435/879 |
| 4,657,849 | 4/1987 | Källenius et al. | 435/7 |
| 4,725,557 | 2/1988 | Miyauchi et al. | 436/543 |
| 4,752,565 | 6/1988 | Folks et al. | 435/5 |
| 4,840,941 | 6/1989 | Ueno et al. | 514/56 |
| 4,863,852 | 9/1989 | Wilkins et al. | 435/7 |
| 4,869,826 | 9/1989 | Wang et al. | 435/176 |

FOREIGN PATENT DOCUMENTS 270317 6/1988 European Pat. Off. .
WO86/04064 7/1986 World Int. Prop. O. .

OTHER PUBLICATIONS

Krivan et al.; Proc. Natl. Acad. Sci. U.S.A., vol. 85, pp. 6157–6161, Aug. 1988 Microbiology.
Krivan et al.; The Jounral of Biological Chemistry, vol. 264, No. 16, Issue of Jun. 5, pp. 9283–9288, 1989.
Roberts et al.; The Jounral of Bilogical Chemistry, vol. 264, No. 16, Issue of Jun. 5, pp. 9289–9293, 1989.
Hakomori; C&EN, Mar. 30, 1981, pp. 23,44–53, 97 & 290.

Primary Examiner—Ronald W. Griffin

[57] ABSTRACT

The invention is a carbohydrate receptor for *Mycoplasma pneumoniae* and *Mycoplasma hominus* and its use to detect mycoplasma in biological fluids and diseased tissue and cells. The receptor can be included in a composition having a pharmaceutically acceptable carrier. Methods are provided for purifying, detecting, or removing mycoplasma from diseased tissue or fluids. The receptor includes sulfatides, dextran sulfate, sialyloligosaccharides, and mixtures thereof.

11 Claims, 9 Drawing Sheets

ADHESION OF MYCOPLASMA PNEUMONIAE AND MYCOPLASMA HOMINUS TO SULFATIDE

FIELD OF THE INVENTION

The present invention relates generally to carbohydrate receptors and their use. Specifically, for the detection of *Mycoplasma pneumoniae* and *Mycoplasma hominus*, a method for removing *Mycoplasma pneumoniae* and *Mycoplasma hominus* from fluids, and for inhibiting the growth of *Mycoplasma pneumoniae* and *Mycoplasma hominus*.

BACKGROUND OF THE INVENTION

Mycoplasmas are a group of microorganisms which are intermediate in size between bacteria and viruses. Included among the human Mycoplasma species which to date have been characterized are *Mycoplasma hominis* types 1 and 2, *Mycoplasma salivarium*, *Mycoplasma fermentans*, *Mycoplasma orale* types 1 and 2, and *Mycoplasma pneumoniae*. The species *M. hominis* type 1 has been recovered from the genitourinary tract, and its frequent occurrence in association with venereal disease, non-bacterial urethritis, cervicitis, and other inflammatory diseases of the genital tract has been reported as well as its association with exudative pharyngitis. *M. pulmonis*, while not indigenous to man, has been isolated from tissue cultures inoculated with specimens from leukemia patients. *M. hominis* type 2, which is occasionally isolated from human specimens, has been shown to be identical to a rodent mycoplasma, *M. arthritidis*.

The rapid identification of mycoplasmas becomes extremely important in initiating the proper treatment of illnesses of which mycoplasmas are the causative agent, especially because they are resistant to many of the antibiotics and chemotherapeutic agents used for bacterial infections.

In recent years, it has been reported that mycoplasmas are present, as contaminants, in tissue cultures such as are used in the metabolic studies of cells or in the propagation of viruses. A prime contaminant has been identified as *M. hominis*, type 1. The occurrence of mycoplasma in tissue cultures furnishes a potential source for an erroneous interpretation of results, since the interpretation invariably presumes that cultures are devoid of microbial contaminants.

Techniques and methods for isolating, identifying, and inhibiting the growth of mycoplasmas, particularly the human strains, therefore have become important in the preparation and use of tissue cultures.

*Mycoplasma pneumoniae* is a small prokaryotic parasite of the human respiratory tract and the etiologic agent of primary atypical pneumonia. This pathogen has no cell wall, and requires exogenous cholesterol for the synthesis of plasma membrane and glucose as a carbon and energy source. In tracheal organ cultures the adhesion of viable mycoplasms to the respiratory epithelium is essential for the initiation of infection (cf. Collier et al., *Infect. Immun.* 3: 694-701, 1971; Hu et al., op. cit. 11: 704-710, 1975; Hu et al. op. cit. 14: 217-224, 1976). Once bound, *M. Pneumonia* does not penetrate the epithelial surface, but causes extensive damage to the tracheal epithelium, leading to ciliostasis, loss of cilia, and finally, cell death (Collier et al., in *Pathogenic Microplasmas*, Ciba Foundation Symposium, Jan. 25 to 27, 1972, Elsevier/North-Holland, Amsterdam, p. 307-327 and Carson et al., *Infect. Immun.* 29: 1117-1124, 1980).

*M. pneumoniae* also binds in vitro to many other eucaryotic cells, including human colon carcinoma cells (WiDr), human lung fibroblasts (MRC5), HeLa cells, hamster tracheal epithelial cells, spermatozoa, and erythrocytes. Some of these studies suggest that sialyl-glycoproteins may be receptors for *M. pneumoniae*, as treatment of the cells with neuraminidase decreases binding (Manchee et al., *Br. J. Exp. Pathol.* 50: 66-75, 1969; Sobeslavsky et al., J. Bacgeriol. 96: 695-705, 1968; and Barile, M. F. in The Mycoplasmas, Vol. II, Tully et al., Eds., pp 425-464, Academic Press, New York, 1979).

Recent studies suggest that the organism recognizes Neu-Ac$\alpha$2- 3Gal$\beta$1-4GlcNAc sequences on erythrocytes, as both glycolipids and glycoproteins containing this structure inhibit adhesion of bacteria, cf. Loomes et al., *Nature (Lond)* 307: 560-563, 1984; and Loomes et al., *Infect. Immun.* 47: 15-20, 1985. Other studies, however, suggest that glycolipids are not receptors for *M. pneumoniae*, cf. Gabridge et al., *Infect. Immun.* 25: 455-459, 1979; and Geary et al., *Isr. J. Med. Sci.* 23: 462-468, 1987.

A number of prior art workers have provided methods for detecting and identifying mycoplasmas. For example, Cekoric et al. in U.S. Pat. No. 3,668,075 disclose a method for identifying groups of mycoplasmas based on the fact that certain heparinoid compounds selectively inhibit the growth of mycoplasmas in growth media.

Makela et al. in U.S. Pat. No. 4,652,518 disclose a preparation for detecting chlamydial infections using a lipopolysaccharide for Re-lipopolysaccharide mutants of gram-negative bacteria. The polysaccharide is complexed to a carrier molecule to enhance immunological response.

Waters et al. in U.S. Pat. No. 4,632,902 disclose a method for detecting biological activity using a nutrient growth medium which isolates antibiotics and other microbial growth inhibitors during culturing of a microorganism. The growth medium contains an isolating substance which isolates antimicrobial materials during culturing of a microorganism. The isolating substances may be ion exchange resins or non-functional adsorbent resins.

Keller et al. in U.S. Pat. No. 4,543,328 disclose a method for separating bacteria, fungi, and viruses from blood during extracorporeal circulation of the blood with a biocompatible adsorbent. These polymers are blood compatible, and may be polyacrylates, polymethacrylates, crosslinked polystyrenes, cellulose acetate, collodium, and nylon.

Japanese patent 55-31959 discloses a latex for diagnosis of *Mycoplasma pneumoniae* infectious diseases comprising a *Mycoplasma pneumoniae* lipid antigen bound with a suspension of latex particles. The lipid antigen may be produced by extracting Mycoplasma fungi bodies with an organic solvent. The *Mycoplasma pneumoniae* strains are cultured and the fungi bodies are collected and extracted with an organic solvent. A sensitized latex is produced by adding a solution containing lipid antigen into a suspension where latex particles are suspended, and treating the resultant mixture for 2-4 hours. The latex sensitized with lipid antigen may be conserved at 4° C. for longer than one hour by adding a protecting agent such as glycine or dextran and freeze-drying.

Schiefer et al. in Soecialia Aug. 15, 1978, p. 1011, disclose that surface carbohydrate structures can be visualized on Mycoplasma membranes using a cytochemical staining procedure with concanavalin A and iron-dextran complexes. However, there is no disclosure that this staining can be used for diagnostic purposes.

SUMMARY OF THE INVENTION

It is an object of the present invention to advance the treatment of Mycoplasma induced disease, and more particularly to provide improvements in the detection of Mycoplasma induced disease.

It is a further object of the present invention to provide receptors that mediate binding of M. pneumoniae means and M. hominus to cells.

It is another object of the present invention to inhibit the adhesion of M. pneumoniae and M. hominus to human cells and tissues.

It is yet another object of the present invention to provide a method for detecting the presence of M. pneumoniae and M. hominus in biological fluids.

It is still another object of the present invention to provide a method for detecting the presence of M. pneumoniae and M. hominus in tissue cultures, According to the present invention, dextran sulfate, but not other presently known sulfated or anionic polysaccharides, completely inhibits binding of M. pneumoniae and M. hominus to purified sulfatide. The dextran sulfate partially inhibits adhesion of M. pneumoniae and/or M. hominus to cultured human colon adenocarcinoma cells.

The presence or absence of M. pneumoniae or M. hominus in a biological sample is determined according to the present invention by contracting the sample with dextran sulfate, and then testing for the presence of M. pneumoniae or M. hominus such as by staining and thin layer chromatography.

Dextran sulfate inhibits the binding of M. pneumoniae and M. hominus to a variety of human cells containing sulfatide receptors, including cells which contain terminal Gal(3SO4)$\beta$1-residues. Since dextran sulfate inhibits the binding of this microorganism to cells, the administration of dextran sulfate to a patient or host infected with this microorganism can prevent the growth and multiplication of this microorganism by inhibiting its binding to human cells.

Because M. pneumoniae in a sample can interfere with analyses for a variety of other substances, it is often desirable to remove the M. pneumoniae from the fluid being tested prior to performing the tests. Either dextran sulfate alone, or a combination of a sialyloligosaccharide, i.e. a compound containing $\alpha$2-3-linked sialic acid, and dextran sulfate is adsorbed onto an insoluble carrier, and the test fluid then contacted with this carrier. The M. pneumoniae then adhere to the carrier, and can be effectively removed from the test fluid.

BRIEF DESCRIPTION OF THE DRAWINGS

FIG. 2 shows binding of M. pneumoniae to purified glycolipids.

FIG. 3 shows the energy and temperature dependent binding of M. pneumoniae to sulfatide.

FIG. 4 shows the inhibition of M. pneumoniae binding to sulfatide by dextran sulfate.

DETAILED DESCRIPTION OF THE INVENTION

Figure 1:
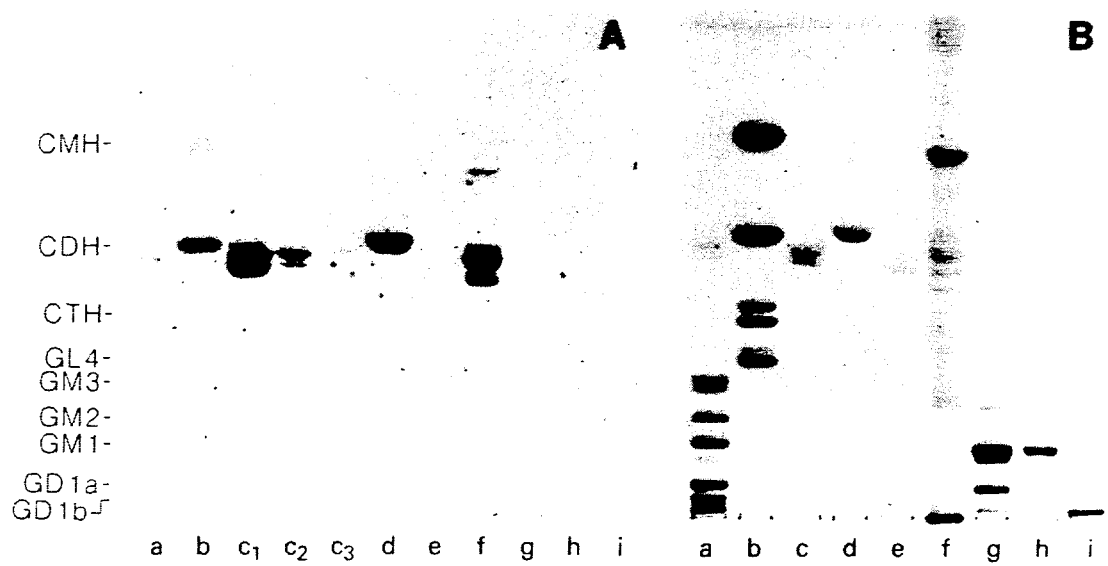
FIG. 1 shows the binding of M. pneumoniae to glycolipids separated by thin layer chromatography.

Dextran sulfate inhibits the binding of M. pneumoniae to a variety of human cells containing sulfatide receptors, including glycolipids such as seminolipid and lactosylsulfatide, which all contain terminal Gal(3SO4)$\beta$1-residues.

According to the present invention, a virulent strain of Mycoplasma pneumoniae was metabolically labelled with [$^3$H]palmitate and studied for binding to glycolipids and to WiDr human colon adenocarcinoma cells. It was found that the organism bound strongly to sulfatide and to other sulfated glycolipids, such as seminolipid and lactosylsulfatide, which all contain terminal Gal(-3SO4)$\beta$1-residues.

M. pneumoniae binds only weakly or not at all to many gangliosides, including the sialylneolacto-series and neutral glycolipids. Only metabolically active M. pneumoniae cells bind to sulfatide, as binding is maximal in RPMI medium at 37° C., and is almost completely abolished in nutrient-deficient medium or by keeping the cells at 4° C.

This is particularly relevant because sulfatide occurs in large amounts in human trachea, lung, and WiDr cells, and the administration of dextran sulfate can thus inhibit binding of the M. pneumoniae to these human cells.

Several purified glycoproteins, including laminin, fetuin, and human chorionic gonadotropin, promote dose-dependent and saturable adhesion of M. pneumoniae when adsorbed on plastic. Adhesion to the proteins is energy dependent, as no attachment occurs in media without glucose. Adhesion to all of the proteins requires sialic acid, and only those proteins with $\alpha$2-3-linked sialic acid are active. The $\alpha$-subunit of human chorionic gonadotropin also promotes attachment, suggesting that a simple biantennary asparagine-linked oligosaccharide is sufficient for binding. Soluble laminin, asparagine-linked sialyloligosaccharides from fetuin, and 3'-sialyllactose but not 6'-sialyllactose inhibit attachment of M. pneumoniae to laminin. M. pneumoniae also bind to sulfatide adsorbed on plastic. Dextran sulfate, which inhibits M. pneumoniae binding to sulfatide, does not inhibit attachment on laminin, and 3'-sialyllactose does not inhibit binding to sulfatide, suggesting that two distinct receptor specificities mediate binding to these two carbohydrate receptors. Both 3'-sialyllactose and dextran sulfate partially inhibit M. pneumoniae adhesion to a human colon adenocarcinoma cell line (WiDr) at concentrations that completely inhibit binding to laminin or sulfatide, respectively, and in combination they inhibit binding of M. pneumoniae to these cells by 90%. Thus, both receptor specificities contribute to M. pneumoniae adhesion to cultured human cells.

Bovine brain sulfatide (galactosyl ceramide-I$^3$-sulfate), ceramide monohexoside, ceramide trihexoside, globoside, and gangliosides GM1 and GD1a were obtained from Supelco. Lactosylceramide and glucosylceramide were obtained from Calbiochem. Other reference gangliosides were obtained from Bachem, Inc. Seminolipid ($\beta$-galactosylalkylacylglycerol-I$^3$-sulfate) was isolated from bovine testes as described by Roberts et al. in *Cancer Res.* 48:3367-3373, 1988. Galactosyl ceramide-I6-sulfate was prepared as described by Roberts et al. in *J. Biol. Chem.* 261: 6972-6977, 1986, by sulfation of galactosyl ceramide. Sulfated glucuronosyl-paragloboside (IV$^3$-[3'SO$_3$GlcA]- nLcOse4Cer) was purified from human peripheral nerve as reported by Chou et al. in *J. Biol. Chem.* 261:11717-11725, 1986. Lactosylceramide-II$^3$-sulfate, GM3, and sialyllactofucopentaosyl-(III)-ceramide were purified from human kidney as described by Rauvala et al in *J. Biol. Chem.* 251:7517-7520, 1976, and Hanfland et al., in *Biochemistry* 20:5310-5319, 1981. α-galactosylparagloboside (IV$^3$GalnLcOse4Cer) and the I-active α-Ga12lactoisooctaosylceramide were purified from rabbit erythrocytes as described by Watanabe et al. in *J. Biol. Chem.* 254: 3221-3228, 1979. Lactoisooctaosylceramide was prepared from the latter lipid by treatment with coffee bean α-galactosidase. Alpha2-3-sialylparagloboside (NeuGc), α2-3-sialyllactoneohexaosylceramide, GM3 (NeuGc), and an I-active ganglioside were prepared from bovine erythrocytes according to the process of Watanabe et al. in *J. Biol. Chem.* 254:8223-8228, 1979. α2-3-sialyl-paragloboside (NeuAc) was isolated from type O human erythrocytes as described by Ardo et al. in *J. Biochem.* 79: 625-632, 1976.

Paragloboside and lactoneohexaosylceramide were prepared by desialylation of the respective gangliosides with 1 M formic acid for sixty minutes at 100° C. Lacto-N-triaosylceramide was prepared by digestion of paragloboside with bovine testes $\beta$-galactosidase.

The identities of the neolacto-series glycolipids was confirmed by immunostaining with monoclonal antibody My-28 before and after neuraminidase digestion. Lipids were extracted from normal human lung, trachea, and WiDr cells and separated into neutral and acidic fractions by anion exchange chromatography on DEAE-Sepharose in the bicarbonate form. For some experiments WiDr cells were metabolically labelled with [$^{35}$S]-sulfate. Cells were removed from the tissue culture flasks by removing the medium and adding 2.5 mM EDTA in 10 mM phosphate buffered saline pH 7.3. After sixty minutes at 37° C., the cells were collected by centrifugation and extracted as described above. The sulfated glycolipids in the tissue extracts were detected by staining of the lipids separated by high performance thin layer chromatography with $^{125}$I-von Willebrand factor.

Growth and Labelling of Organisms

Virulent *M. pneumoniae* strain M129, passage 5-15, were grown and metabolically labelled with [$^3$H]palmitic acid, 12-17 Ci/mole, as described by Chandler et al. in *Infect. Immun.* 37: 942, 1982. The organisms were passed four times through a 26 gauge needle and suspended to approximately 10$^7$ cpm/ml of degassed RPMI 1640 medium containing 1% bovine serum albumin and 25 mM HEPES, pH 7.3.

Mycoplasma Overlay Assay

*M. pneumoniae* were bound to glycolipids separated on thin-layer chromatograms as described in detail for other bacteria by Krivan et al., *Proc. Natl. Acad. Sci.* 85: 6157-6161, 1988, and Krivan et al., *Arch. Biochem. Biophys.* 260:493-496, 1988. Briefly, glycolipids were separated by thin-layer chromatography on aluminum-backed silica gel high-performance plates developed with chlooform:methanol:0.25% CaCl$_2$ in water (60:35:8). After chromatography, the plates were coated with 0.1% polyisobutylmethacrylate, soaked in 0.05 M Tris-HCl, pH 7.6, containing 110 nM sodium chloride, 5 mM CaCl$_2$, 0.2 mM phenylmethane-sulfonyl fluoride, and 1% bovine serum albumin (TBS-BSA) and incubated for three hours at 25° C. with 60 μl/cm$^2$ of [$^3$H]-labelled *M. pneumoniae*, approximately 10$^7$ cpm/ml of RPMI-BSA. The plates were gently washed five times in 0.01 M sodium phosphate, pH 7.2, containing 0.15 M sodium chloride (PBS) to remove unbound organisms, dried, and exposed for 24 hours to Ultrofilm $^3$H (2208-190) high speed film.

Solid-Phase Binding Assay

The binding of *M. pneumoniae* to purified glycolipids immobilized in microtiter plates was measured as described by Krivan et al. in *Proc. Natl. Acad. Sci.*, op. cit. Purified glycolipids were serially diluted in 25 μl of methanol containing 0.1 μg each of the auxiliary lipids cholesterol and phosphatidylcholine. After the solutions were dried by evaporation, the wells were filled with TBS-BSA, emptied after one hour, rinsed with RPMI-BSA, and incubated with 25 μl of [$^3$H]-*M. pneumoniae*, approximately 10$^7$ cpm/ml RPMI-BSA. After incubation for two hours at 37° C., unless otherwise stated, the wells were washed five times with saline and bound *M. pneumoniae* was quantified by scintillation counting in Aquasol. For inhibition studies, various polysaccharides were serially diluted in 25 ml of [$^3$H]-*M. pneumoniae*.

Mycoplasm adhesion to cultured cells

Adhesion of [$^3$H]-*M. pneumoniae* to cells on glass covered slips was measured by a modification of a method previously described by Chandler et al., *Infect. Immun.*, op. cit. WiDr human colon adenocarcinoma, ATCC CCL 218 was grown in Eagle's minimal essential medium with 10% fetal calf serum in a 5% CO$_2$ atmosphere at 37° C. The cells were removed with trypsin and plated on 12 mm round glass coverslips in 24-well tissue culture plates and grown for three days. Control coverslips were preincubated in medium without cells. The coverslips were washed in serum-free medium, then incubated in RPMI-BSA for fifteen minutes. The medium was removed and labelled *M. pneumoniae* suspended in 0.5 ml of RPMI-BSA were added to each well. The plates were incubated on a rocking table for 60 minutes at 37° C. The coverslips were washed by dipping in saline six times, and the bound radioactive bacteria were determined by scintillation counting. For inhibition studies, the inhibitors were added to *M. pneumoniae* prior to adding the bacteria to the coverslips.

Binding of *M. pneumoniae* to Glycolipids on Thin Layer chromatograms

Incubation of [$^3$H]-labelled *M. pneumoniae* with various glycolipids resolved on thin layer chromatograms was used to determine the carbohydrate binding specificity of the organism. As shown by an autoradiogram, FIG. 1A, compared with a similar thin layer plate visualized with orcinal reagent, FIG. 1B, *M. pneumoniae* bound avidly to authentic sulfatide, detecting 100 ng of this glycolipid, lane C3, and to a glycolipid with the same mobility as sulfatide in the acidic lipid fraction of human trachea, lane f. This tracheal glycolipid was confirmed to be sulfatide by its specific staining with $^{125}$I-labelled von Willebrand factor. Sulfatide was also detected in human lung lipids but at lower levels than in trachea.

M. pneumoniae also bound to other sulfated glycolipids including lactosyl sulfatide and seminolipid, which contain the same terminal Gal(3SO$_4$)$\beta$1-residue as sulfatide, and an isomer of sulfatide in which the terminal sulfate is linked to the 6-position of galactose. Table 1 shows the structures of interest.

M. pneumoniae also binds to high amounts of lactosylderamide and to a lesser extent glucosylceramide, paragloboside, and o-galactosylparagloboside, but not to other neutral glycolipids, as shown in Table 1. No binding was detected to other acidic glycolipids including $\alpha$2-3-sialylparagloboside, I-active monosialylganglioside, or to the gangliosides GM3, GM2, GM1, GD1a, GS1b, and GT1b. In addition, sulfate itself is not sufficient for binding, as M. pneumoniae does not bind to high amounts of cholesterol sulfate or to sulfated glucuronosylparagloboside, which has a terminal sulfate linked to the 3-position of glucuronic acid.

To obtain the results shown in FIG. 1, glycolipids were chromatographed on aluminum-backed silica gel HPTLC plates developed in chloroform/methanol/0.25% CaCl$_2$ in water, 60:35:8. The plates were coated with plastic, soaked in Tris-BSA, and incubated for three hours at 25° C. with [$^3$H]-palmitate-labelled M. pneumoniae suspended in RPMI 1640 containing 1% BSA and 25 mM HEPES, pH 7.3, as described above (Panel A), or sprayed with orcinol reagent to identify glycolipids (Panel B). Lane a, acidic glycolipid standards sulfatide (0.5 $\mu$g), GM3 (2 $\mu$g), GM2 (2 $\mu$g), GD1a (2 $\mu$g), GD1b (2 $\mu$g), GT1b (2 $\mu$g); lane b, neutral standards galactosyl ceramide (4 $\mu$g), lactosylceramide (4 $\mu$g), globotriaosylceramide (2 $\mu$g), c2(0.5 $\mu$g), and c3 (o.1 $\mu$g); lane d, seminolipid (2 $\mu$g); lane e, cholesterol 3-sulfate (2 $\mu$g); lane f, human trachea acidic glycolipids from 100 mg wet weight of bovine erythrocytes; lane h, $\alpha$2-3sialylparagloboside (2 $\mu$g); lane 1, I-active monosialylganglioside from bovine erythrocytes (2 $\mu$g).

Figure 2:
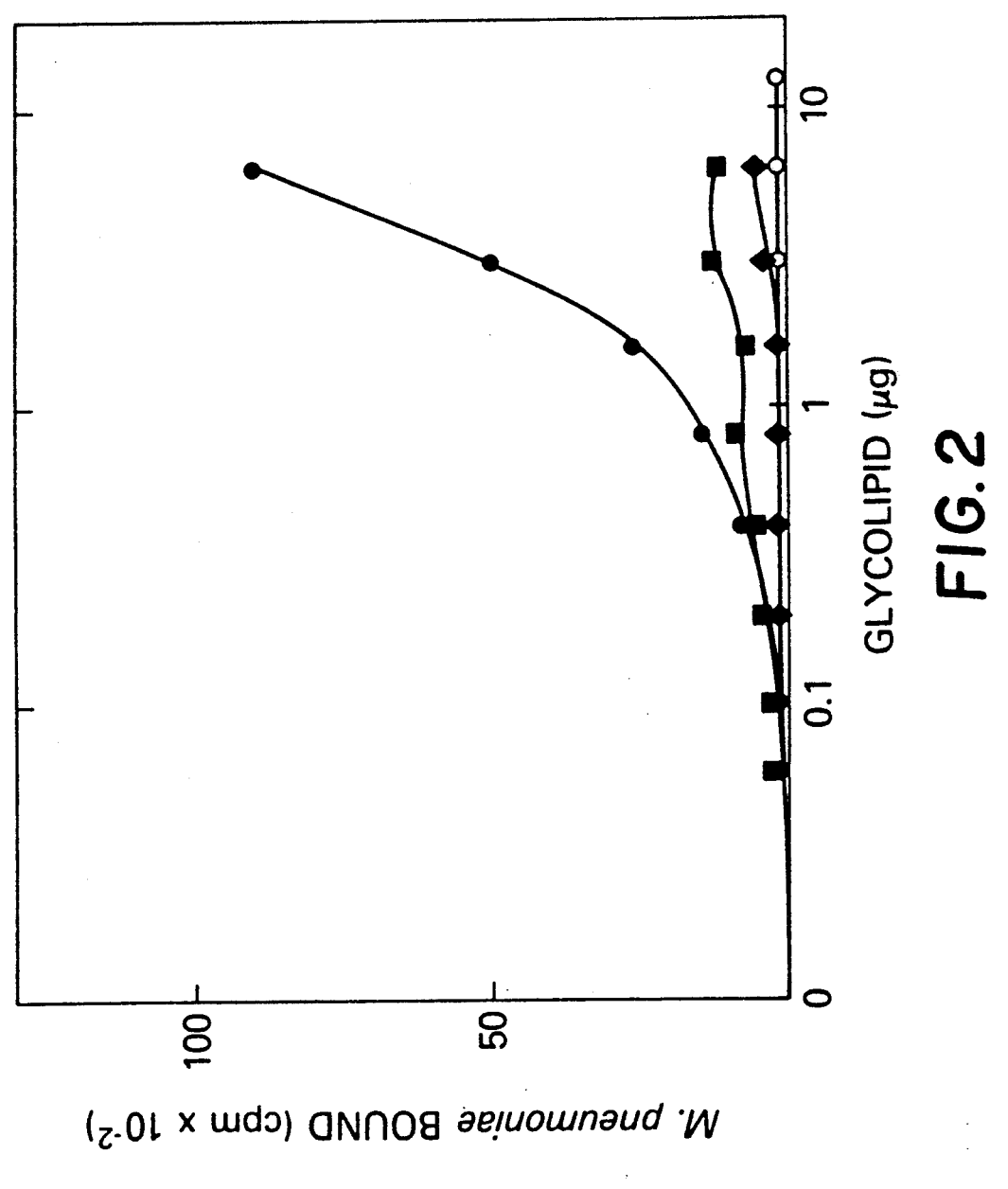

Quantitative Binding of M. pneumoniae to Immobilized Glycolipids in Microtiter Plates Binding of M. pneumoniae to purified glycolipids adsorbed on microtiter plates was examined to further define binding specificity. Binding to sulfatide was sensitive and dose-dependent, as shown in FIG. 2. M. pneumoniae bound weakly to lactosylceramide and paragloboside, whereas no binding was detected to cholesterol sulfate or other glycolipids tested at 10 $\mu$g per well, consistent with the data obtained from the overlay assay.

Figure 3:
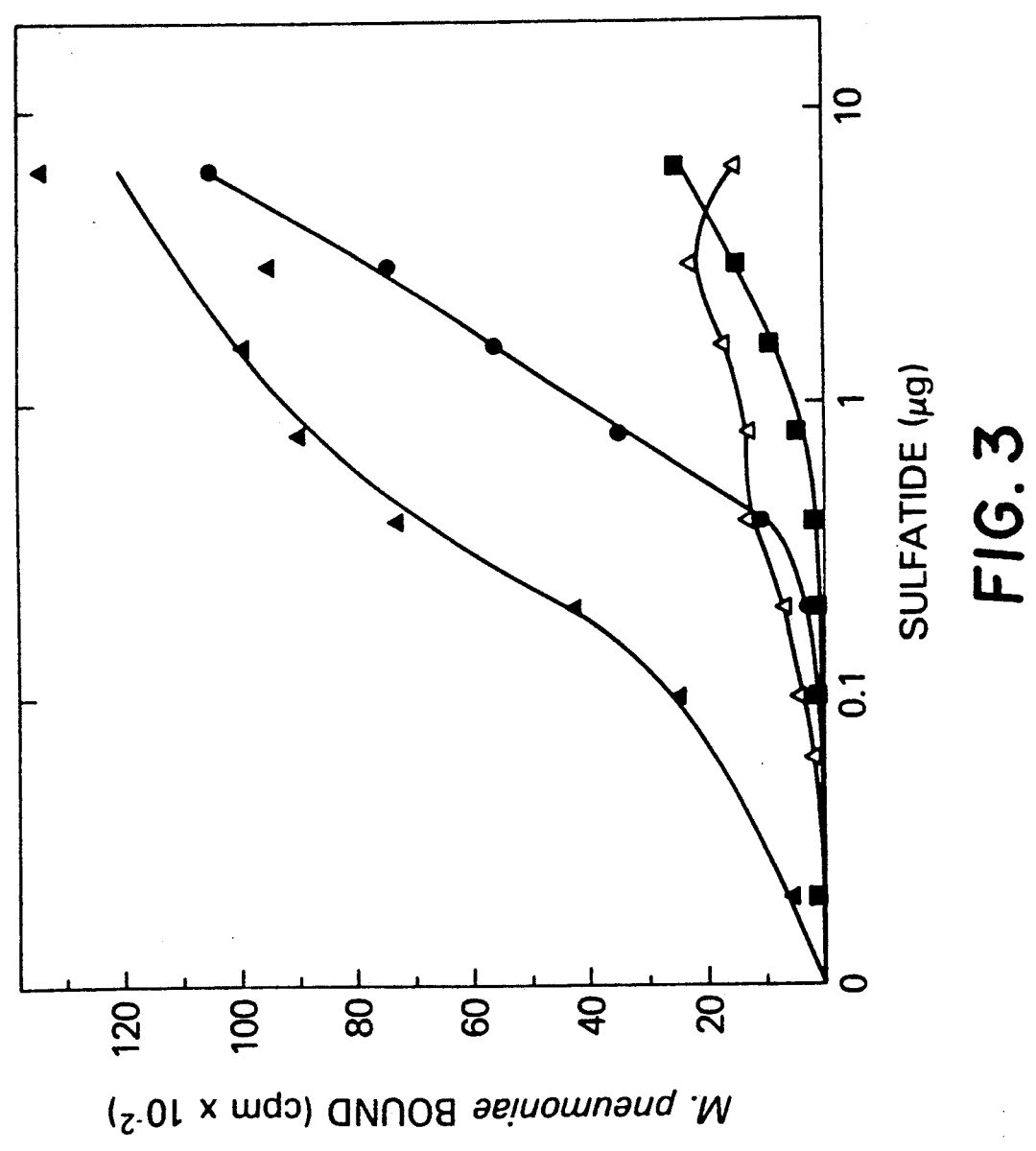

Binding of M. pneumoniae to sulfatide is both energy and temperature dependent, as shown in FIG. 3. At 37° C. about 0.25 $\mu$g of sulfatide was required for half-maximum binding. The binding activity was about five times lower at 25 C and was minimal at 4° C. M. pneumoniae also bound poorly at 37° C. in nutrient-deficient medium (Tris-BSA without RPMI) with binding activities comparable to that obtained at 4° C., as shown in FIG. 3. These results suggest that M. pneumoniae requires energy and physiological temperatures for maximal binding to occur.

To obtain the results shown in FIG. 2, lipids in 25 $\mu$g each of the auxiliary lipids cholesterol and phosphatidylcholine were evaporated in flat bottom wells of polyvinylchloride microtiter plates. The wells were blocked with 1% albumin for one hour, washed twice with RPMI-BSA, and incubated at 25° C. with 25 $\mu$l of [$^3$H]-M. pneumoniae, approximately 105 cpm. After two hours, the wells were washed five times with saline, cut from the plate, and bound radioactivity was quantified in a scintillation counter. In control experiments, organisms were incubated with auxiliary lipids only to correct for nonspecific binding, typically <1% of the total radioactivity added. M. pneumoniae binding was determined in RPMI-BSA for sulfatide (●), lactosylceramide (■), paragloboside (♦), and cholesterol sulfate, ceramide trihexoside, globoside, GM1, GM2, or GM3 (○).

In FIG. 3, to demonstrate the energy and temperature dependent binding of M. pneumoniae to sulfatide, microtiter wells were coated with sulfatide and blocked with albumin as described for FIG. 2. Binding of [$^3$H]-M. pneumoniae was determined in RPMI-BSA for two hours at 4° C. (■), 25° C. (●), 37° (▲), and at 37° C. in BSA without RPMI (Δ). Inhibition of M. pneumoniae Binding to Immobilized Sulfatide and WiDr Monolayers by Dextran Sulfate.

Figure 4:
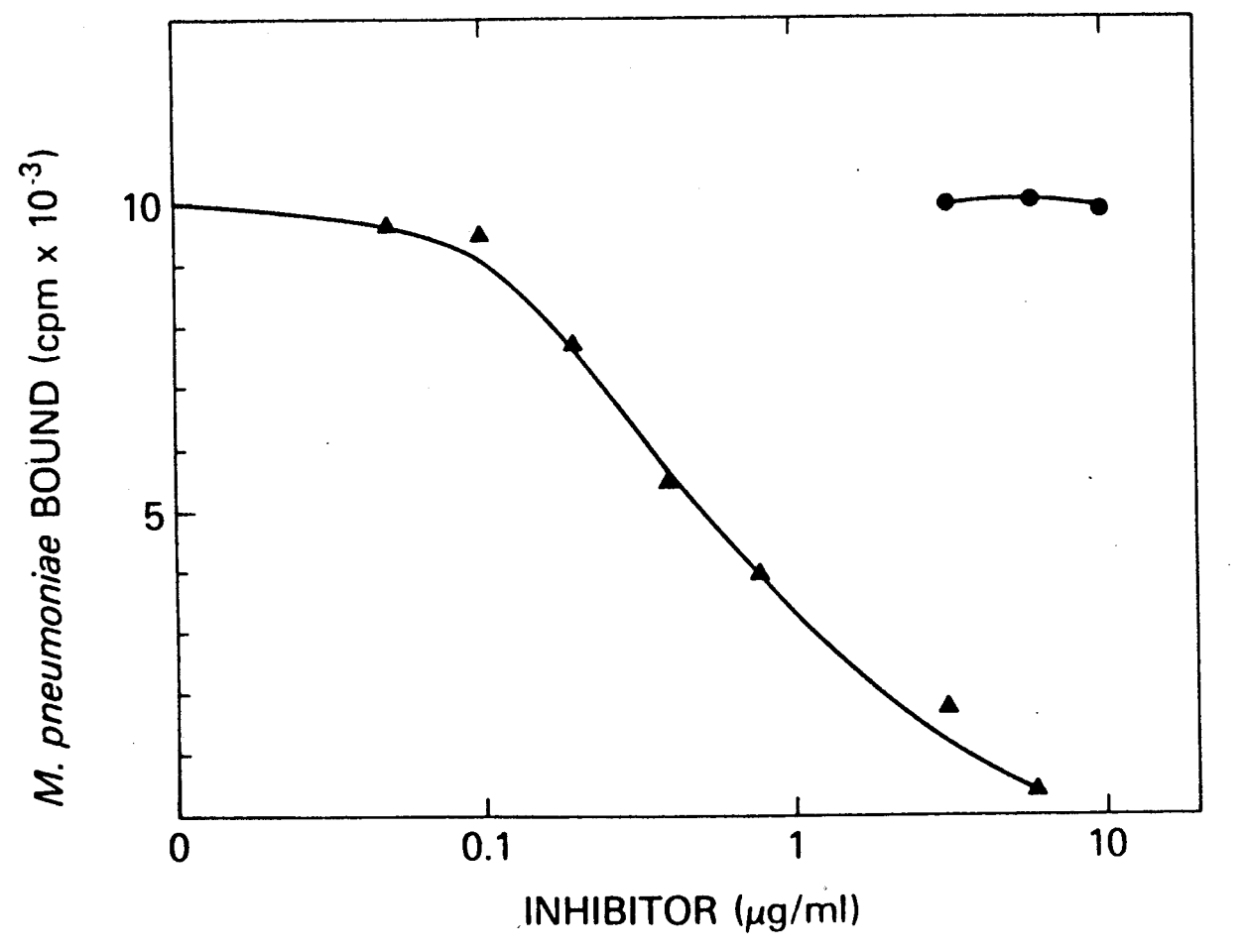

Various anionic polysaccharides were tested for inhibition of M. pneumoniae binding to sulfatide adsorbed in microtiter plates, as shown in FIG. 4. Dextran sulfate at 0.4 $\mu$g/ml inhibited binding to 1 $\mu$g of sulfatide by 50%, whereas dextran had no effect. At 100 $\mu$g/ml yeast phosphomannan, colominic acid, hyaluronate, and several sulfated polysaccharides such as fucoidin, heparin, and chondroitin sulfate did not inhibit binding.

To obtain the results shown in FIG. 4, polysaccharides were serially diluted in 25 $\mu$l of RPMI-BSA in microtiter wells previously coated with 1 $\mu$g of purified sulfatide. Binding was determined after incubation of two hours at 37° C. with 25 $\mu$l of [$^3$H]-M. pneumoniae with the indicated concentration of dextran (●) or dextran sulfate (▲).

Because virulent strains of M. pneumoniae adhere to mammalian cells, monolayers of WiDr cells were used to determine if dextran sulfate inhibits adhesion of the organism. [$^3$H]- labelled M. pneumoniae was incubated with WiDr cell monolayers attached to coverslips in triplicate with an without dextran sulfate, as shown in Table II. Dextran sulfate inhibited adhesion in all three experiments, but the degree of inhibition varied between experiments. In each experiment, 10 $\mu$g/ml dextran sulfate inhibited more than 1 $\mu$g/ml, but 100 $\mu$g/ml dextran sulfate caused no further inhibition. Thus, maximal inhibition was obtained with approximately 10 $\mu$g/ml of dextran sulfate. Similar results were obtained with MRC5 lung fibroblasts where in three experiments a mean of 47% of M. pneumoniae adhesion was inhibited by dextran sulfate.

TABLE I

| Glycolipids tested for ability to bind M. pneumoniae | | |
|---|---|---|
| Name[a] | Structure | Binding[b] |
| Sulfatide | Gal(3SO$_4$)$\beta$1—1Cer | +++ |

TABLE I-continued

Glycolipids tested for ability to bind M. pneumoniae

| Name[a] | Structure | Binding[b] |
|---|---|---|
| Sulfatide | Gal(6SO$_4$)$\beta$1—1Cer | +++ |
| Lactosylsulfatide | Gal(3SO$_4$)$\beta$1—4Glc$\beta$1—1Cer | +++ |
| Seminolipid | Gal(3SO$_4$)$\beta$1—3alkylacylglycerol | +++ |
| Glucosylcer (CMH) | Glc$\beta$1—1Cer | + |
| Lactosylcer (CDH) | Gal$\beta$1—4Glc$\beta$1—1Cer | ++ |
| Lacto-N-triaosylcer | GlcNAc$\beta$1—3Gal$\beta$1—4Glc$\beta$1—1Cer | + |
| Paragloboside | Gal$\beta$1—4GlcNAc$\beta$1—3Gal$\beta$1—4Glc$\beta$1—1Cer | + |
| $\alpha$-Galactosylparagloboside | Gal$\alpha$1—3Gal$\beta$1—4GlcNAc$\beta$1—3Gal$\beta$1—4Glc$\beta$1—1Cer | + |
| Galactosylcer (CMH) | Gal$\beta$1—1Cer | — |
| SO$_4$-Glucuronosylparagloboside | GlcA(3SO$_4$)$\beta$1—3Gal$\beta$1—4GlcNAc$\beta$1—3Gal$\beta$1—4Glc$\beta$1—1Cer | — |
| Trihexosylcer (CTH) | Gal$\alpha$1—4Gal$\beta$1—4Glc$\beta$1—1Cer | — |
| Asialo GM2 | GalNAc$\beta$1—4Gal$\beta$1—4Glc$\beta$1—1Cer | — |
| Globoside (GLA) | GalNAc$\beta$1—3Gal$\alpha$1—4Gal$\beta$1—4Glc$\beta$1—1Cer | — |
| Asialo GM1 | Gal$\beta$1—3GalNac$\beta$1—4Gal$\beta$1—4Glc$\beta$1—1Cer | — |
| GM3 | NeuAc$\alpha$2—3Gal$\beta$1—4Glc$\beta$1—1Cer | — |
| GM3 (NeuGc) | NeuGc$\alpha$2—3Gal$\beta$1—4Glc$\beta$1—1Cer | — |
| GM2 | GalNAc$\beta$1—4[NeuAc$\alpha$2—3]Gal$\beta$1—4Glc$\beta$1—1Cer | — |
| GM1 | Gal$\beta$1—3GalNAc$\beta$1—4[NeuAc$\alpha$2—3]Gal$\beta$1—4Glc$\beta$1—1Cer | — |
| Sialylparagloboside | NeuAc$\alpha$2—3Gal$\beta$1—4GlcNAc$\beta$1—3Gal$\beta$1—4Glc$\beta$1—1Cer | — |
| Sialylparagloboside (NeuGc) | NeuGc$\alpha$2—3Gal$\beta$1—4GlcNAc$\beta$1—3Gal$\beta$1—4Glc$\beta$1—1Cer | — |
| Sialylneolactofucopentaosylcer | NeuAc$\alpha$2—3Gal$\beta$1—4[Fuc$\alpha$1—3]GlcNAc$\beta$1—3Gal$\beta$1—4Glc$\beta$1—1Cer | — |
| GD1a | NeuAc$\alpha$2—3Gal$\beta$1—3GalNAc$\beta$1—4[NeuAc$\alpha$2—3]Gal$\beta$1—4Glc$\beta$1—1Cer | — |
| GD1[b] | Gal$\beta$1—3GalNAc$\beta$1—4[NeuAc$\alpha$2—8NeuAc$\alpha$2—3]Gal$\beta$1—4Glc$\beta$1—1Cer | — |
| GT1b | NeuAc$\alpha$2—3Gal$\beta$1—3GalNac$\beta$1—4[NeuAc$\alpha$2—8NeuAc$\alpha$2—3]Gal$\beta$1—4Glc$\beta$1—1Cer | — |
| Sialylneolactohexaoslycer | NeuGc$\alpha$2—3Gal$\beta$1—4GlcNAc$\beta$1—3Gal$\beta$1—4GlcNAc$\beta$1—3Gal$\beta$1—4Glc$\beta$1—1Cer | — |
| I-Active Sialyllactoisooctaosylcer | Gal$\alpha$1—3Gal$\beta$1—4GlcNAc$\beta$1\\_6\\Gal$\beta$1—4GlcNAc$\beta$1—3Gal$\beta$1—4Glc$\beta$1—1Cer / NeuAc$\alpha$2—3Gal$\beta$1—4GlcNAc$\beta$1/3 | — |
| I-active Lactoisooctaosylcer | Gal$\beta$1—4GlcNAc$\beta$1\\_6\\Gal$\beta$1—4GlcNAc$\beta$1—3Gal$\beta$1—4Glc$\beta$1—1Cer / Gal$\beta$1—4GlcNAc$\beta$1/3 | — |
| I-active Gal$_2$-lactoisooctaosylcer | Gal$\alpha$1—3Gal$\beta$1—4GlcNAc$\beta$1\\_6\\Gal$\beta$1—4GlcNAc$\beta$1—3Gal$\beta$1—4Glc$\beta$1—1Cer / Gal$\alpha$1—3Gal$\beta$1—4GlcNAc$\beta$1/3 | — |

[a]Trivial names and structures are represented according to recomendations in ref. 47 and references cited therein; cer, ceramide.
[b]Negative binding (—) indicates no binding to 4 $\mu$g of lipid and positive binding to less than 0.5 $\mu$g (+++), 0.5 to 2 $\mu$g (++), and 2–4 $\mu$g (+).

TABLE II

Inhibition of M. pneumoniae adherence to adenocarcinoma cell monolayers (WiDr) by dextran sulfate

| Dextran Sulfate ($\mu$g/ml) | $^3$H-M. pneumoniae attached (% of control)[a] | | |
|---|---|---|---|
|  | Exp. 1 | Exp. 2 | Exp. 3 |
| 1 | 69 | 83 | 89 |
| 10 | 19 | 77 | 74 |
| 100 | 31 ($p < 0.002$) | 78 ($p < 0.05$) | 72 ($p < 0.1$) |

[a]Results are the average of triplicate determinations normalized to control binding in the absence of inhibitor: 7%, 21%, and 11% of the added mycoplasma respectively for the three experiments. Nonspecific binding to medium-treated coverslips without cells was 2–3% of the total added. The significance of the inhibition at 100 $\mu$g/ml dextran sulfate, relative to the control adhesion to WiDr cells in the absence of inhibitor, was determined using a two-sided t test.

Figure 5:
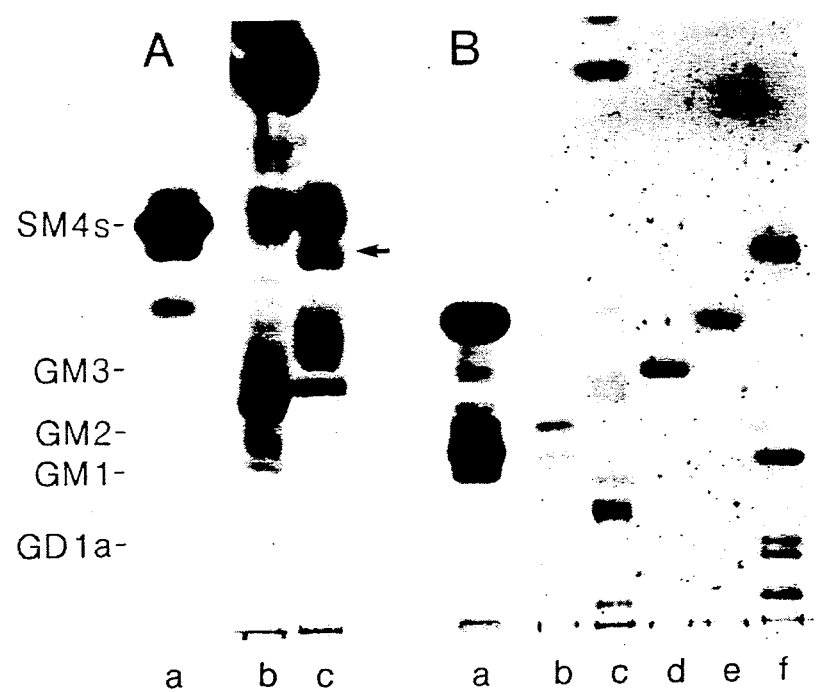
FIG. 5 shows the identification of sulfatide synthesized by WiDr adenocarcinoma cells.

Metabolic labelling with [$^{35}$S]-sulfate confirmed that WiDr cells make a large amount of sulfatide, as shown in FIG. 5. An orcinol-positive resorcinol-negative glycolipid that comigrates with authentic brain sulfatide is detected in acidic lipids from WiDr cells, FIG. 5A, lane c. This lipid contains [$^{35}$S], FIG. 5A, lane 1, and was verified to be sulfatide by comigration with authentic sulfatide in an acidic solvent system that resolves sulfatide, seminolipid, and cholesterol-3-sulfate, FIG. 5B, lane a. Based on incorporation of [$^{35}$S]under steady state labelling, WiDr cells contain approximately 90 nmoles sulfatide per gram wet weight of cells. Significant label was also incorporated into cholesterol 3-sulfate and small amounts into a lipid that comigrates with seminolipid, FIG. 5B, lane a.

To obtain the results shown in FIG. 5, WiDr cells were metabolically labelled with [$^{35}$S]--sulfate as described above. Neutral and acidic lipids were chromatographed on silica gel high performance thin layer plates developed in chloroform/methanol/0.25% KCl in water, 5:4:1 (Panel A) or chloroform/methanol/acetone/acetic acid/water, 8:2:4:2:1 (panel B). The lipids were detected by autoradiography, lane a, or orcinol reagent, lanes b-f.

In Panel A, [$^{35}$S]-labelled acidic lipids from 106WiDr cells, lane a, neutral, lane b, and acidic, lane c, lipids from 30 mg wet weight of WiDr cells. The orcinol positive sulfatide band is indicated by the arrow (→). Migration of reference glycolipids is indicated in the left margin: sulfatide, GM3, GM2, GM1, GD1a, GD1b, and GT1b.

In Panel B, [$^{35}$S]-labelled acidic lipids from 106WiDr cells, lanes a and c, bovine brain sulfatide, lane e, and neutral glycolipid standards from top to bottom: CMH, CDH, CTH, and GL4, lane f.

The glycolipid binding specificity of *M. pneumoniae* was established by the thin layer overlay assay. Of the many glycolipids present on the chromatogram, as shown in Table I, *M. pneumoniae* bound only to sulfated glycolipids and weakly to lactosylceramide, glucosylceramide, lactotrihexaosylceramide, paragloboside, and o-galactosylparagloboside, as shown in FIG. 1. Binding curves of purified sulfatide and lactosylceramide, however, demonstrated that only sulfatide exhibited a good dose response, whereas lactosylceramide bound *M. pneumoniae* weakly and the other glycolipids not at all, as shown in FIG. 2. Interestingly, *M. pneumoniae* does not discriminate between galactosyl ceramide $I^3$-sulfate and its unnatural 6-sulfate isomer, cf. Table 1, yet the organism does not bind to cholesterol sulfate or to sulfated glucuronosylparagloboside, which has a terminal sulfate linked to the 3-position of glucuronic acid. These results indicate that sulfate alone is not sufficient for *M. pneumoniae* binding and that at least $Gas(3SO_3)\beta 1$-residues in glycolipids are required.

*M. pneumoniae* did not bind to =2-3-sialylneolactoseries glycolipids either on thin layer chromatograms or adsorbed in cholesterol-phosphatidylcholine on microtiter plates. This finding appears to be at variance with reports that these glycolipids as well as brain gangliosides, which lack the noelacto-series core structure, inhibit adhesion of *M. pneumoniae*, and the finding of the present inventors that the organism binds to asparagine-linked oligosaccharides bearing this terminal structure. However, as demonstrated for laminin-mediated hemagglutination and laminin binding to sulfatide, inhibition by gangliosides may be indirect in that they mask sulfatide receptors. It is postulated that mannose, which occurs in asparagine-linked glycoproteins but is absent in glycolipids, may be required for tight binding.

The biological relevance for sulfatide for adhesion of *M. pneumoniae* is suggested by three findings. First, only metabolically-active *M. pneumoniae* cells bind to sulfatide, as is shown in FIG. 3. At physiological temperatures, binding was maximal in RPMI medium and almost completely abolished in nutrient-deficient medium or at temperatures of 4° C. These results are consistent with the finding of others that adhesion of *M. pneumoniae* is decreased by metabolic poisons, low temperatures, and by using nonviable organisms, and that adhesion may be influenced by an energized membrane. Second, sulfatide occurs in high amounts in human trachea and is present in human lung and cultured WiDr human colon adenocarcinoma cells, as shown in FIGS. 1 and 5. The latter have approximately 50 million sulfatide molecules per cell. Additional sulfated glycoconjugates that are recognized by *M. pneumoniae* may be present on glycoproteins or proteoglycans in these tissues. Thirdly, dextran sulfate, which specifically inhibits sulfatide-dependent binding, partially inhibits *M. pneumoniae* adhesion to WiDr cells.

The existence of receptors other than sialylglycoproteins would explain why inhibition of *M. pneumoniae* binding to cultured cell lines by sialylglycoconjugates or following neuraminidase treatment is usually incomplete. This is also the case with inhibition studies in which 1 μg/ml dextran sulfate completely abolished binding to purified sulfatide immobilized on plastic, as shown in FIG. 4, but only partially inhibited *M. pneumoniae* adhesion to WiDr cells, cf. Table 2. Thus, there are probably at least two distinct receptors that mediate binding of *M. pneumoniae* to cells: glycolipids containing terminal NeuAcα2-2Galβ1-4GlcNAc sequences, both of which must be blocked for complete inhibition of *M. pneumoniae* binding to cultured cells. Sulfatide-mediated adhesion may be important in mycoplasma pathogenicity to guarantee intimate contact of the parasite with the host membrane to satisfy its strict nutritional requirements.

Adhesion of *M. pneumoniae* to many cell types in vitro may be mediated by recognition of sialyloligosaccharides on the host cell surface. Based on selective restoration of binding or beuraminidase-treated erythrocytes using CMP-sialic acid and purified sialyltransferases, adhesion of the erythrocytes on surface grown sheet cultures of *M. pneumoniae* specifically requires sialic acid linked α2-3 to N-acetyllactosamine sequences. Inhibition studies using glycolipids, glycoproteins, and oligosaccharides suggested that sialylated linear or branched polylactosamine sequences on both glycoproteins and glycolipids are receptors an erythrocytes for *M. pneumoniae.* Although glycolipids including gangliosides inhibited attachment in this and several other adherence assays, cf. Chandler et al., *Infect. Immun.* 38: 598–603, 1982; other workers have concluded that binding is mediated by glycoproteins but not glycolipids, cf. Gabridge et al., *Infect. Immun.* 25: 455–459, 1979 and Geary et al., *Isr. J. Med. Sci.* 23: 462–468, 1987. In the latter study, no sialic acid was found in a purified receptor protein from lung fibroblast (MRC5) cells.

It has now been found that several glycoproteins containing α2-3 but not α2-6 linked sialic acid can support attachment of *M. pneumoniae* and that simple biantennary asparagine-linked oligosaccharides are sufficient to efficiently mediate adhesion. Based on inhibition studies, this binding specificity is distinct from sulfatide binding and both mechanisms are involved in adhesion to cultured human cells.

*M. pneumoniae* Adhesion to Immobilized Glycoproteins

Glycoproteins dissolved in 0.01 M sodium phosphate buffer, pH 7.4, containing 150 mM NaCl, 1 mM $CaCl_2$, and 0.01% $NaN_3$ were adsorbed onto plastic polyvinylchloride 86 well microtiter plates by incubation for 16 hours at 4° C. The unbound proteins were removed, and the wells were filled with tris-BSA and incubated for 30 minutes at room temperature. The wells were rinsed with RPMI1640 containing 25 mM HEPES, pH 7.3, and 1% bovine serum albumin. *M. pneumoniae* strain M129 labelled with [$^3$H]-palmitate were dispersed in RPMI-BSA by passing four times through a 26 gauge needle, and 50 μl of the suspension was applied to the wells. After incubation for 60 minutes at 37° C., the wells were washed five times with saline and the labelled *M. pneumoniae* bound to the proteins were quantified by scintillation counting in Aquasol.

For inhibition studies, sugars in 25 μl of RPMI-BSA were added to wells coated with 10 μg/ml laminin followed by 25 μl of [$^3$H]-*M. pneumoniae.* Binding was determined to both laminin-coated and uncoated wells in triplicate at each inhibitor concentration and in the absence of inhibitor. In some experiments, the adsorbed proteins were pretreated with neuraminidase. After adsorption of the proteins and incubation in tris-BSA, the wells were rinsed three times with 50 mM sodium acetate, pH 5.5, containing 150 mM NaCl, 5 mM $CaCl_2$, 1 mg/ml bovine serum albumin, and 1 mM phenylmethanesulfonyl fluoride. The wells were incubated with 0.05 units/ml neuraminidase in the same buffer or with buffer without enzyme overnight at 20° C. The wells were rinsed three times with tris-BSA, and *M. pneumoniae* binding was determined as described above.

Binding of monoclonal antibody My-28 to the immobilized proteins before or after digestion with neuraminidase was determined using a 1:1000 dilution of ascites fluid in tris-BSA. After incubation for two hours at room temperature, the wells were washed three times with tris-BSA. Bound antibody was detected using goat anti-mouse IgM labelled with $^{125}$I by the Iodogen method.

*M. pneumoniae* Adhesion to WiDr Cells

Figure 6:
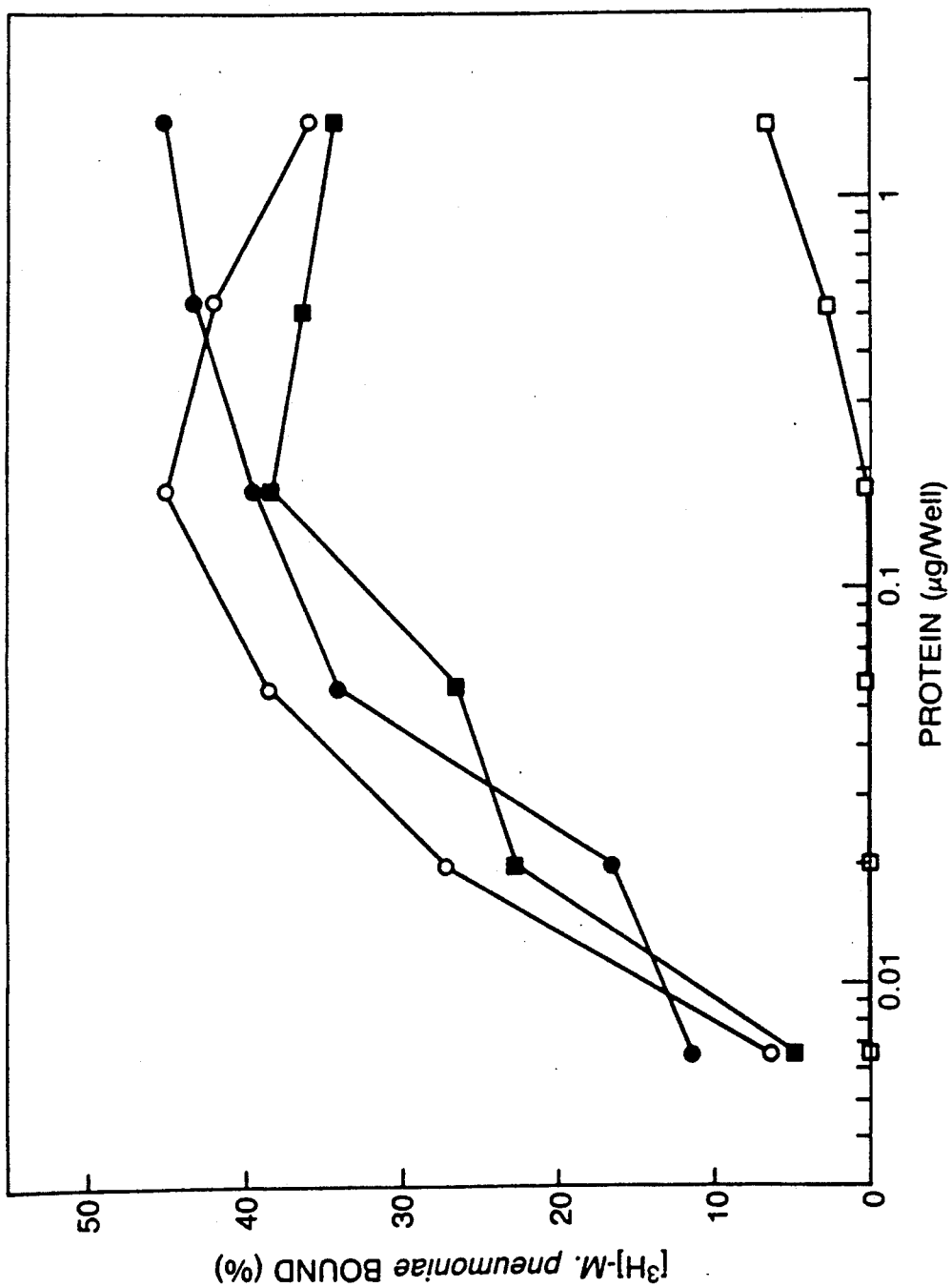
FIG. 6 shows M. pneumoniae binding to immobilized glycoproteins

Adhesion of labelled *M. pneumoniae* to WiDr cells on glass cover slips was determined as described previously. For inhibition studies, dextran sulfate and 3'-sialyllactose were dissolved in RPMI-BSA and the pH was adjusted to 7.4 with NaOH. The inhibitors were added to wells containing washed cover slips with attached WiDr cells or blank cover slips preincubated in medium or tris-BSA. Labelled *M. pneumoniae* were added immediately and incubated with slow rocking for sixty minutes at 37° C. After the coverslips were washed by dipping six times in saline, bound *M. pneumoniae* were determined by scintillation counting in Aquasol. In FIG. 6, [$^3$H]-labelled *M. pneumoniae*, 630,000 cpm/5×10$^5$ CCU, were incubated in microtiter wells coated in duplicate with laminin (●), fetuin (○), hCG (■), or transferrin (□) at the indicated concentrations. After washing to remove the unbound organisms, the bound mycoplasma were determined by scintillation counting. Binding to uncoated wells was 3% of the applied radioactivity.

Several glycoproteins including laminin, fetuin, and hCG support dose dependent and saturable adhesion of *M. pneumoniae* when adsorbed on plastic, as shown in FIG. 6. Typically, 20 to 60% of the added *M. pneumoniae* bound to the wells at saturating protein concentrations. Nonspecific binding to uncoated wells was 0.3 to 3% of the total radioactivity applied. Binding is energy dependent, and no binding was detected in a tris-albumin buffer without glucose. Most proteins, however, are inactive in this assay, as shown in FIG. 6 and Table III. The relative activities of several proteins for promoting *M. pneumoniae* adhesion were estimated by comparing the dose response curves, and are summarized in Table III. The proteins laminin, fetuin, thrombospondin, hCG, and the alpha-subunit of hCG have similar activity and promote adhesion to wells coated with less than 10 ng of glycoprotein. Glycophorin and alpha-1-acid glycoprotein are weakly active, whereas the other proteins are essentially inactive, promoting binding of less than 10% of the added *M. pneumoniae* at the highest levels tested, 1-5 µg/well.

Immunolon 2 microtiter plates and bacteriological polystyrene were also examined as substrates for *M. pneumoniae* adhesion to adsorbed proteins. Although binding varied with the plastic used, the distinction between the active and inactive glycoproteins was consistently observed with all three types of plastic. Thus, the differences in activity are probably not an artifact of selective adsorption of the active glycoproteins.

Figure 7:
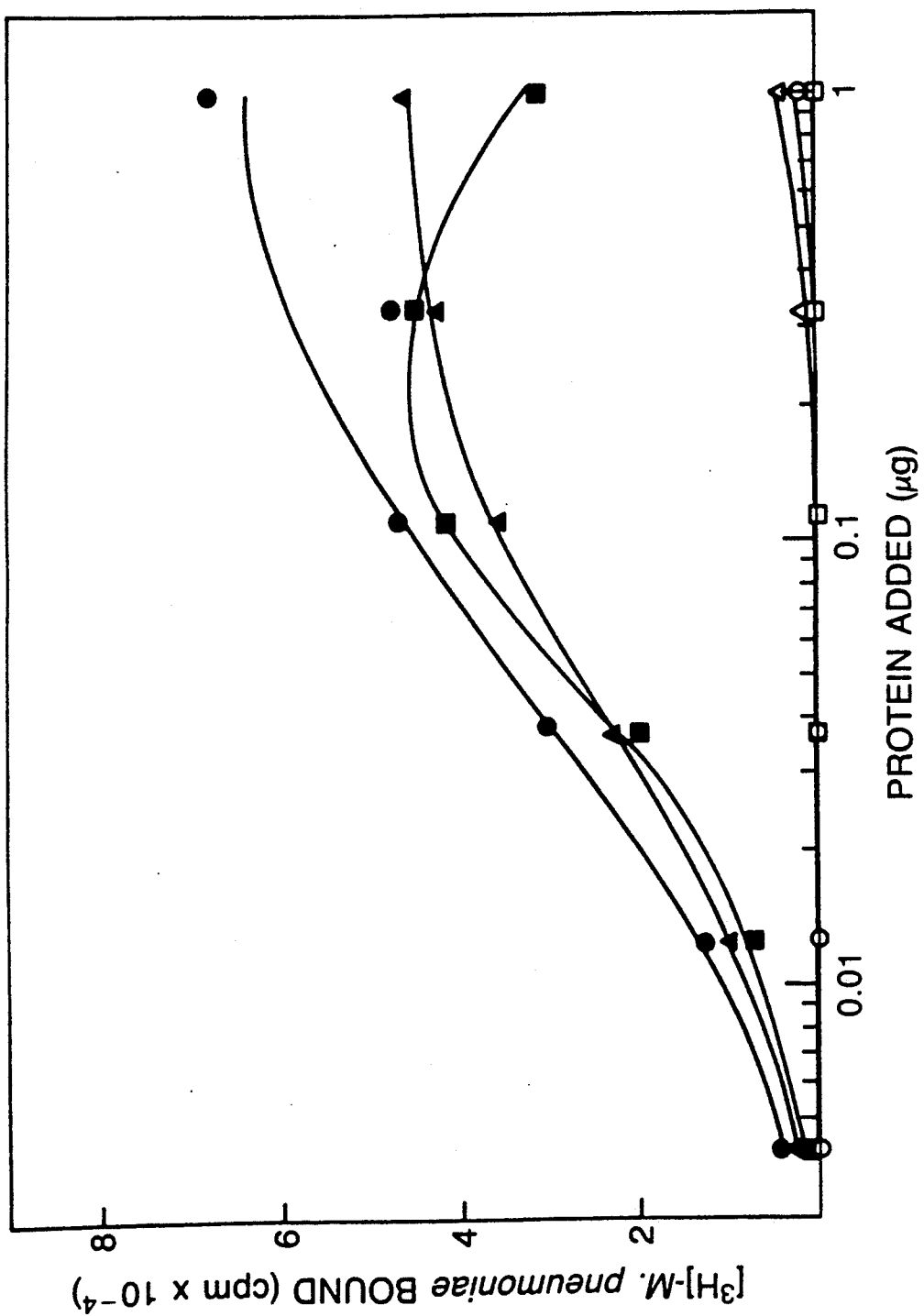
FIG. 7 shows the effect of neuramidase treatment on M. pneumoniae binding to immobilized glycoproteins.
Figure 8:
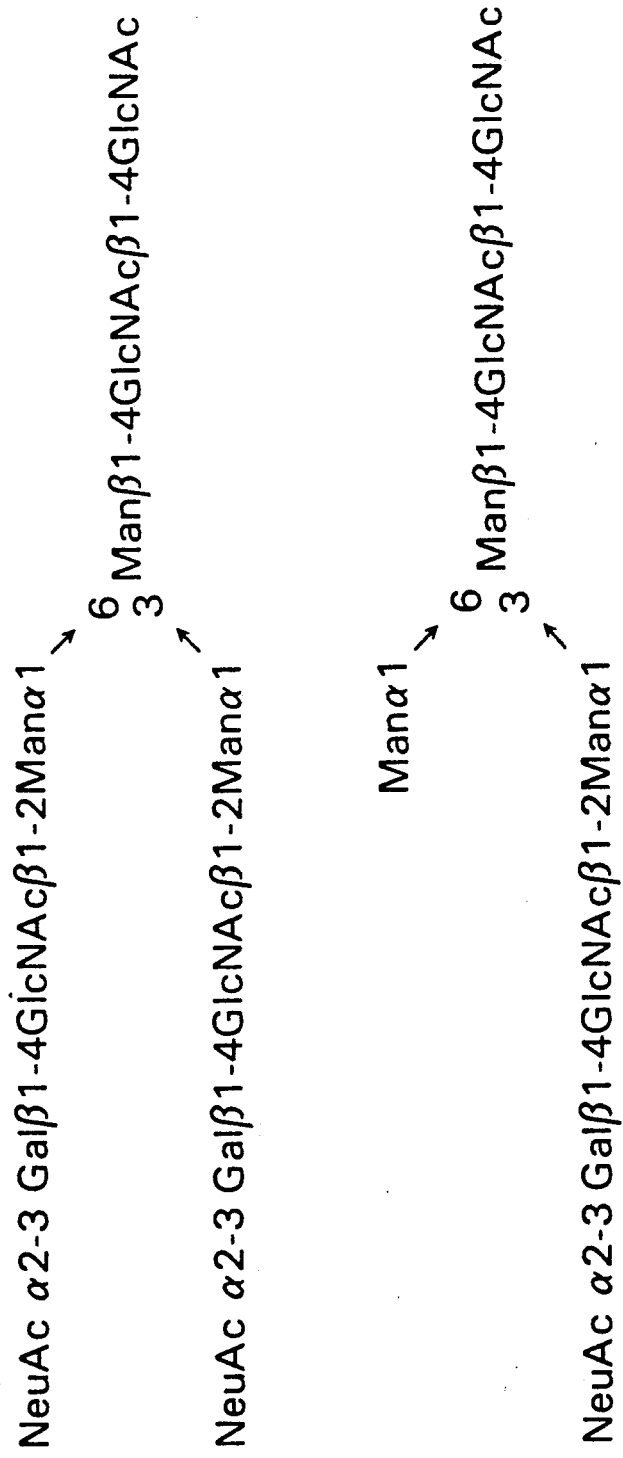
FIG. 8 shows the structures of sialylated oligosaccharides on the $\alpha$ subunit of human chorionic gonadotropin that mediates M. pneumoniae adhesion.

FIG. 7 illustrates the effect of neuraminidase treatment on *M. pneumoniae* binding to immobilized glycoproteins. Microtiter wells were coated with fetuin (circles), hCG (squares), or α-subunit of hCG (triangles) and treated for sixteen hours with 0.05 U/ml neuraminidase (Closed symbols) in sodium acetate buffer, pH 5.5, or buffer alone (open symbols). [$^3$H]-labelled *M. pneumoniae* binding was determined as described above.

Binding to the active glycoproteins requires sialic acid, as neuraminidase treatment of the adsorbed protein as shown in FIG. 7 or pretreatment with neuraminidase in solution before adsorption (results not shown) abolishes all binding activity. Several of the inactive glycoproteins also contain silaic acid, but the linkage reported in human transferrin, fibrinogen, and plasma fibronectin is exclusive α2-6 to galactose. The linkage in hCG and a majority of N-linked fetuin oligosaccharides is α2-3. Thus, in agreement with previous studies of erythrocyte adhesion to surface grown sheet cultures of *M. pneumoniae*, binding of the labelled *M. pneumoniae* to immobilized glycoproteins appears to be specific for α2-3-linked sialic acid.

With the exception of hCG, all of the active glycoproteins have extensive heterogeneity in their carbohydrate structure or have only partially characterized structure. HCG contains only mono- and biantennary asparagine-linked oligosaccharides on both subunits and four O-linked oligosaccharides on the β-subunit. Since the α-subunit of hCG binds *M. pneumoniae* as well as the intact protein, as shown in Table III and FIG. 7, the O-linked carbohydrates on the β-subunit are not required for binding. Thus, a biantennary asparagine linked carbohydrate with α2-3-linked sialic acid is sufficient for binding of *M. pneumoniae*.

TABLE III

*M. pneumoniae* binding to glycoproteins adsorbed on plastic

| Protein | Relative binding activity[a] |
| --- | --- |
| Murine Laminin | 1.5 |
| Bovine Fetuin | 1.0 |
| hCG | 0.7 |
| hCG α-subunit | 0.8 |
| Human platelet thrombospondin | 0.7 |
| Human type MM glycophorin | 0.06 |
| Human α$_1$-acid glycoprotein | 0.03 |
| Hen Ovomucoid | <0.01 |
| Human Transferrin | <0.01 |
| Human plasma Fibrinogen | <0.01 |
| Human plasma Fibronectin | <0.01 |
| Bovine serum Albumin | <0.01 |

[a]Binding of [$^3$H]-*M. pneumoniae* was determined to polyvinyl chloride microtiter wells coated with 0.006 to 2 µg of the respective proteins. Relative binding activities of the proteins were determined by the amount of protein required to give half maximal binding of mycoplasma and are expressed relative to fetuin which was assigned a value of 1.0. Results are the mean values of 2 or 3 experiments.

Inhibition of binding after neuraminidase treatment is not due to a contaminating protease as all of the adsorbed proteins bind monoclonal antibody My-28 after neuraminidase treatment. This antibody recognizes N-acetyllactosamine sequences found in glycolipids and glycoproteins. In most cases, antibody binding is detected only after neuraminidase digestion. Excepting glycophorin, which binds about ten-fold less antibody, all of the asialoglycoproteins have similar binding curves with antibody My-28. Uniform binding of the antibody to all of the neuraminidase-treated glycoproteins confirms that all of the proteins are adsorbed on plastic to a similar extent under the conditions used, and that sialylated N-acetyllactosamine sequences on the immobilized proteins are accessible for binding antibodies and *M. pneumoniae*.

Binding of *M. pneumoniae* to adsorbed laminin is inhibited by soluble laminin with 50% inhibition as 80 µg/ml, as shown in Table IV. Binding is also inhibited by 3'-sialyllactose at comparable concentrations. 6'-

Sialyllactose is at least ten-fold less active. Neither laminin nor 3'-sialyllactose inhibits *M. pneumoniae* attachment to sulfatide. Conversely, dextran sulfate is a potent inhibitor of binding to sulfatide, but has no effect on attachment on laminin. Thus, the two binding specificities probably require two independent carbohydrate binding sites on the *M. pneumoniae* pathogen.

Asparagine-linked oligosaccharides released from fetuin also inhibit *M. pneumoniae* binding to laminin, as shown in Table IV. Unfractionated oligosaccharides and the unbound fraction from chromatography on concanavalin A-Sepharose have similar inhibitory activity to 3'-sialyllactose. The latter fraction contains the triantennary oligosaccharides of fetuin. The bound fraction from the concanavalin-A column, which should contain the biantennary oligosaccharides of fetuin, is about 20-fold more active, inhibiting *M. pneumoniae* binding by 50% at 12 μM.

TABLE IV

Inhibition of *M. pneumoniae* binding to laminin or sulfatide adsorbed on plastic

| Inhibitor | Substrate | |
|---|---|---|
| | Laminin | Sulfatide |
| | I.D.$_{50}$[a] | |
| 3'-sialyllactose | 0.3 mM | >5 mM |
| 6'-sialyllactose | >5 mM[b] | N.D. |
| Fetuin oligosaccharides Con A unbound | 0.3 mM | N.D. |
| Fetuin oligosaccharides Con A bound | 0.012 mM | N.D. |
| laminin | 80 μg/ml | >200 μg/ml |
| dextran sulfate | >200 μg/ml[c] | 0.5 μg/ml |

[a]Concentration of inhibitor giving 50% inhibition of control binding. Oligosaccharide concentrations are presented as sialic acid concentrations determined by the periodate-resorcinol assay (12).
[b]Binding was 54% of control at 5 mM inhibitor.
[c]Binding was 112% of control at 200 μg/ml dextran sulfate Mr 500,000.

Figure 9:
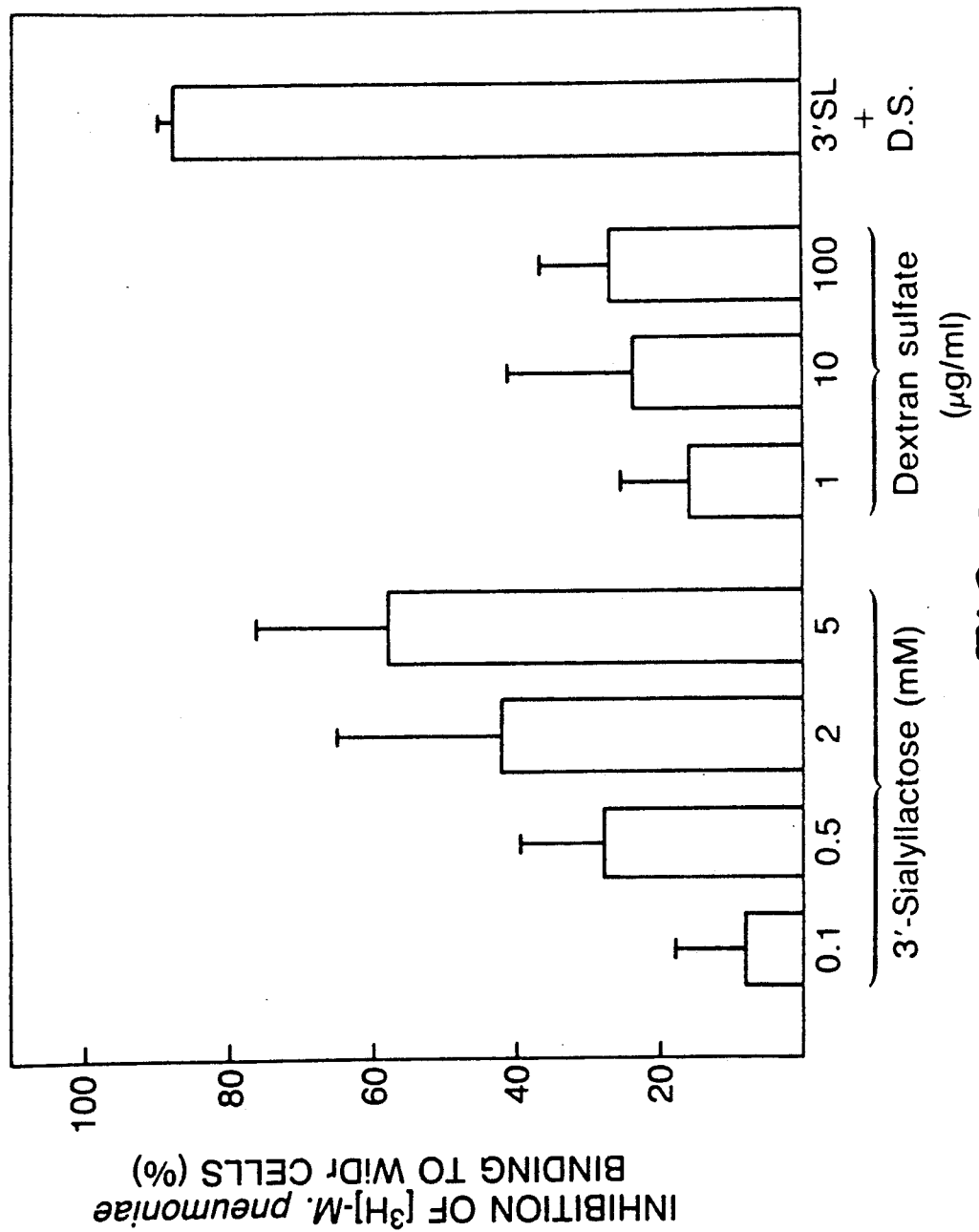
FIG. 9 shows the inhibition of M. pneumoniae adhesion to human adenocarcinoma cell lines (WiDr).

FIG. 9 shows the inhibition of *M. pneumoniae* adhesion to human adenocarcinoma cell line (WiDr). Adhesion of [$^3$H]-*M. pneumoniae* to WiDr cells growing on 13 mm glass cover slips was determined as described above. Inhibition by dextran sulfate or 3'-sialyllactose at the indicated concentrations was calculated relative to control binding determined in RPMI/BSA without inhibitors. The results are presented as percent inhibition (mean±S.D. n=4 with n=8 for determination of control binding without inhibitor).

3'-Sialyllactose inhibits *M. pneumoniae* adhesion to monolayers of WiDr cells. The inhibition is dose dependent, but at concentrations more than ten-fold higher than the ID$_{50}$ for inhibiting binding to laminin, 40% of the control adhesion remains. In the same experiment, dextran sulfate also gave partial inhibition of *M. pneumoniae* adhesion. However, when the two inhibitors were combined, adhesion was inhibited by 90%. Thus, both binding specificities participate in adhesion to WiDr cells and complete inhibition of *M. pneumoniae* adhesion to these cells can be achieved using a combination of inhibitors for both binding mechanisms.

As can be seen from the above, the adhesive glycoproteins laminin and thrombospondin and several other glycoproteins, when adsorbed on plastic, strongly promote adhesion of *M. pneumoniae*. The adhesive activities of all of these proteins depends on sialic acid on their oligosaccharides, and is lost after neuraminidase treatment. All or most of the sialic acid on these proteins is linked $\alpha$2-3 to galactose. In human plasma fibronectin and fibrinogen and except for a minor triantennary oligosaccharide in transferrin, all sialic acid is linked $\alpha$2-6, and no binding of *M. pneumoniae* was detected. Thus, the specific requirement for $\alpha$2-3-linked sialic acid for binding to purified glycoproteins is in agreement with previous results for adhesion of erythrocytes to *M. pneumoniae.*

Whereas the oligosaccharide structures on some of the active glycoproteins are heterogeneous or only partially characterized, the o-subunit of hCG contains only one monoantennary and one biantennary asparagine-linked oligosaccharide, and is as active as the other glycoproteins with more complicated oligosaccharide structures. Therefore, the minimum structure for adhesion of *M. pneumoniae* is probably a simple biantennary oligosaccharide with sialic acid linked $\alpha$2-3 to the terminal galactoses. Strong inhibition by sialyl biantennary oligosaccharides from fetuin but not the triantennary oligosaccharides suggest that this is the preferred structure for *M. pneumoniae* binding. This is a common structure that is probably present on the surface glycoproteins of many cells and could account for the broad range of cell types that show sialic acid-dependent *M. pneumoniae* binding.

The same terminal sequence that is found on the asparagine-linked oligosaccharides of the glycoproteins that bind *M. pneumoniae,* Sial$\alpha$2-3Gal$\beta$1-4GlcNAc$\beta$-, occurs on glycolipids yet does not support binding of *M. pneumoniae* when the glycolipids are immobilized on thin layer plates or in a phosphatidyl choline/cholesterol monolayer on plastic. The orientation of the sequence may be different in glycolipids so that it is not recognized or sterically inhibited from binding *M. pneumoniae,* or additional sugar residues such as the mannose found only on the glycoproteins may be required for high avidity binding.

Although some have proposed that polylactosamine sequences are required for *M. pneumoniae* binding, neither fetuin, thrombospondin, nor hCG has polylactosamine sequences, although laminin does have these sequences. Furthermore, human $\alpha$1 acid glyco-protein has polylactosamine sequences, but they are uncommon in glycophorin and neither protein binds *M. pneumoniae* well. This contrasts with the finding that the latter two proteins inhibit erythrocyte adhesion to *M. pneumoniae* better than fetuin, cf. Loomes et al., *Nature* (*Lond*): 307: 560–563, 1984. Glycophorin contains hydrophobic regions; however, inhibition of sialic acid-dependent erythrocyte binding and invasion by merozoites of Plasmodium falciparum malaria results from a toxicity of the hydrophobic peptide of glycophorin. A similar toxicity may account for inhibition of *M. pneumoniae* adhesion, as a "receptor" for glycophorin was isolated from *M. pneumoniae* membranes but its binding was inhibited as well by a hydrophobic peptide of glycophorin which lacks carbohydrate as by the intact glycophorin.

The ability of fetuin to bind *M. pneumoniae* when adsorbed on plastic is interesting since fetuin is a major protein in fetal calf serum, which is a component of the growth medium for most of the cell types that have been used for attachment assays. Thus, fetuin may adsorb onto the glass substrates or onto the surface of WiDr and other cells and account for all or part of the sialic acid-dependent adhesion. "Non-specific" adhesion of *M. pneumoniae* to coverslips preincubated in medium containing fetal calf serum is specifically inhibited by 3'-sialyllactose but not by dextran sulfate. 3'-Sialyllactose, however, does not inhibit nonspecific binding to coverslips preincubated in tris-BSA.

The inhibition studies tabulated in Table IV indicate that *M. pneumoniae* has two distinct adhesins that recognize sulfated glycolipids and α2-3-linked sialyl oligosaccharides on glycoproteins, respectively. Based on the complete dependence on erythrocyte sialyloligosaccharides for binding, only the latter receptor is required for binding erythrocytes. Inhibition of *M. pneumoniae* adhesion to cultured cell lines by an inhibitor of sulfatide binding or following neuraminidase treatment, however, is usually incomplete. As shown in FIG. 9, the effects of 3'-sialyllactose and dextran sulfate are additive and nearly complete inhibition is obtained with both inhibitors, suggesting that both types of carbohydrates are utilized by *M. pneumoniae* to adhere to these cells in vitro. Based on these results, it is unlikely that agents inhibiting binding to either carbohydrate receptor could prevent infection by blocking adhesion to host epithelium, but a combination of the two types of inhibitors may prevent infection by *M. pneumoniae*.

*Mycoplasma pneumoniae* have been found to bind specifically to glycolipids that contain sulfated esters of galactose, particularly as sulfatide and lactosylsulfatide, and this binding can be specifically inhibited in vitro by dextran sulfate. Thus, dextran sulfate or the Gal(-$SO_4$)$\beta$1-sequence immobilized onto insoluble carriers or supports can be used in agglutination or enzyme-linked assays to specifically detect *M. pneumoniae* or *M. hominus* in body fluids or other solution. The Gal($3SO_4$)$\beta$1-sequence or dextran sulfate can be used to remove *M. pneumoniae* or *M. hominus* from body fluids or other fluids, and to affinity purify components on the bacterial cell that mediate attachment to host tissue in the infection process.

In order to treat a patient infected with *Mycoplasma hominus* or *Mycoplasma pneumoniae*, the dextran sulfate or compound carrying the $SO_3$--Gal-$\beta$-1-Ceramide sequence is combined with a pharmaceutically acceptable carrier and administered to a patient in amount sufficient to bind the pathogen and remove it from the system of the patient. These amounts, which are readily determined by those skilled in the art, can range from approximately 0.1 gram to about 5 grams per patient per day until there is evidence of successful treatment of the infection.

Compositions within the scope of the invention include compositions wherein the active ingredient is contained in an effective amount to achieve its intended purpose. Determination of the effective amount is, of course, within the skill in the art.

In addition to the active Mycoplasma binding compound, the pharmaceutical compositions according to the present invention may contain suitable pharmaceutically acceptable carriers comprising excipients and auxiliaries which facilitate processing of the active ingredients into preparations which can be used pharmaceutically to treat infection with the Mycoplasma pathogens.

Preferably, the preparations, particularly those which can be administered orally and which can be used for the preferred type of administration, such as tablets, dragees, and capsules, and preparations which can be administered rectally, such as suppositories, as well as suitable solutions for administration orally or by injection, contain from about 0.1 to about 99 percent, and preferably from about 25-85 percent, of active ingredient, together with the excipient.

The pharmaceutical preparations of the present invention are manufactured in a manner which is itself known, such as by means of conventional mixing, granulating, dragee-making, dissolving or lyophilizing. The pharmaceutical preparations for oral use can be obtained by combining the active ingredients with solid excipients and processing the compounds, after adding suitable auxiliaries, if desired or necessary, to obtain tablets or dragee cores.

Suitable excipients include fillers such as sugars, for example, lactose, sucrose, mannitol, or sorbitol, cellulose preparations and/or calcium phosphates, such as tricalcium phosphate or calcium hydrogen phosphate, as well as binders such as starch paste using starches such as maize starch, wheat starch, rice starch, potato starch, gelatin, gum tragacanth, methyl cellulose, hydroxypropylcellulose, sodium carboxymethylcellulose, and/or polyvinylpyrrolidone. If desired, disintegrating agents may be added, such as the above-mentioned starches and carboxymethyl starch, crosslinked polyvinyl pyrrolidone, agar, alginic acid or a salt thereof, such as sodium alginate. Auxiliaries are, above, all, flow-regulating agents and lubricants, such as silica, talc, stearic acid or salts thereof, and/or polyethylene glycol. Dragee cores are provided with suitable coatings which, of desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds in a suppository base. Suitable suppository bases are, for example natural or synthetic triglycerides, paraffin hydrocarbons, polyethylene glycols or higher alkanols. In addition, it is also possible to use gelatin rectal capsules which consists of a combination of the active compounds with a base. Possible base materials include, for example, liquid triglycerides, polyethylene glycols, or paraffin hydrocarbons.

Suitable formulations for parenteral administration and irrigation of diseased tissues include aqueous solutions of the active ingredients in water-soluble form. In addition, suspensions of the active ingredients as appropriate oily injection suspensions may be administered. Suitable lipophilic solvents or vehicles include fatty oils, such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension contains stabilizers.

The manner in which detection methods are conducted using the receptors of the present invention will be readily appreciated by persons skilled in the art. A protein which contains sialyloligosaccharide receptors, such as fetuin, is immobilized onto a solid carrier, such as polystyrene beads. Any *Mycoplasma hominus* or *Mycoplasma pneumoniae* present in a test fluid will bind with the sialyloligosaccharide receptors on the carrier. The presence of the Mycoplasma is then detected by an enzyme-dextran sulfate conjugate in a rapid ELISA technique, or by latex agglutination.

Compositions prepared according to the present invention are used to treat patients infected with one of the Mycoplasma pathogens, such as *M. pneumoniae* or *M. hominus*. A composition according to the present invention is administered to the patient for the duration of appearance of symptoms of infection. This time period is determined without undue experimentation by one skilled in the art. Determination of infection can be accomplished by detecting the pathogens in sample of bodily fluid from the patient or from examining the clinical symptoms of infection, such as fever, shivering, etc.

Diseased tissue can be irrigated with a liquid composition containing the dextran sulfate or compound containing the $SO_3$--$\beta$1-1Gal sequence to remove any Mycoplasma pathogens from the tissue. Preferably, a dilute solution containing approximately 0.1 to 5 grams per liter of the active ingredient is contained in a pharmaceutically acceptable carrier, such as saline solution. Irrigation of the tissue is continued until there appear to be no further pathogens present in the tissue.

The dextran sulfate or other $SO_3$-$\beta$1-1Gal-sequence containing compound may alternatively be immobilized onto an insoluble carrier, such as polystyrene beads, glass cover plates, or the like, and used in agglutination or enzyme-linked assays to detect *M. pneumoniae* or *M. hominus* in body fluids or other solutions.

Additionally, dextran sulfate or other compound containing the $SO_3$-$\beta_1$-1Gal-sequence may be immobilized on a suitable carrier and used to remove these bacteria from body fluids so as not to interfere with other assays. The compound is adsorbed onto a carrier and introduced into the fluid, whereby the *M. pneumoniae* or *M. hominus* adhere to the carrier and the carrier containing the bacteria is removed from solution.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

what is claimed is:

1. A receptor which is capable of binding to *Mycoplasma hominus* and *Mycoplsma pneumoniae* comprising a compound selected from the group consisting of compounds containing the structure $SO_3{}^-$-Gal$\beta$1-1Ceramide.

2. A receptor according to claim 1 wherein said compound containing the structure $SO_3{}^-$-Gal$\beta$1-1Ceramide is selected from the group consisting of sulfatides and sialyloligosaccharides.

3. A pharmaceutical composition comprising the receptor according to claim 1 in a pharmaceutically acceptable carrier.

4. The composition according to claim 3 wherein said pharmaceutically acceptable carrier is soluble in water.

5. The composition according to claim 3 wherein said pharmaceutically acceptable carrier is insoluble in water.

6. A method for removing a pathogen selected from the group consisting of *Mycoplasma hominus* and *Mycoplasma pneumoniae* from a sample, comprising contacting said sample with a receptor according to claim 1, incubating said sample with said receptor for a sufficient period of time to bind said sample to said receptor, and removing said receptor from said sample.

7. The method according to claim 6 wherein said receptor is carried on a solid, water-insoluble carrier.

8. A method for treating a patient infected with a pathogen selected from the group consisting of *Mycoplasma hominus* and *Mycoplasma pneumoniae* comprising administering to said patient an effective amount of a composition according to claim 3.

9. A method for detecting a pathogen selected from the group consisting of *Mycoplasma pneumoniae* and *Mycoplasma hominus* comprising:
immobilizing fetuin onto a suitable carrier;
contacting a sample to be analyzed with the immobilized fetuin;
and detecting the presence of the pathogen using an enzyme-dextran sulfate conjugate.

10. A method of preventing infection in a host by a pathogen selected from the group consisting of *Mycoplasma pneumoniae* and *Mycoplasma hominus* comprising administering to a host an effective amount of a composition according to claim 3.

11. A method for treating diseased tissues which is infected with a pathogen selected from the group consisting of *Mycoplasma pneumoniae* and *Mycoplasma hominus* comprising contacting said diseased tissues with a composition according to claim 3.

* * * * *